United States Patent [19]
van Eerdenburg

[11] Patent Number: 5,669,875
[45] Date of Patent: Sep. 23, 1997

[54] ENDOSCOPIC SURGICAL APPARATUS WITH LONGITUDINAL ACTUATION

[75] Inventor: Nicole van Eerdenburg, Voorburg, Netherlands

[73] Assignee: United States Surgical Corporation, Norwalk, Conn.

[21] Appl. No.: 634,314

[22] Filed: Apr. 16, 1996

[51] Int. Cl.⁶ .................................................. A61B 173/32
[52] U.S. Cl. ............................ 604/22; 606/205; 606/170
[58] Field of Search ............................ 606/167–170, 606/174, 205–207, 39, 208–211, 51, 52, 83; 604/22; 128/750–755

[56] References Cited

U.S. PATENT DOCUMENTS

| | | | |
|---|---|---|---|
| 4,590,936 | 5/1986 | Straub et al. | 606/170 X |
| 4,598,711 | 7/1986 | Deniga | 606/207 |
| 4,644,651 | 2/1987 | Jacobsen | 30/251 |
| 4,777,948 | 10/1988 | Wright | 30/341 |
| 5,040,715 | 8/1991 | Green et al. | |
| 5,084,057 | 1/1992 | Green et al. | |
| 5,100,420 | 3/1992 | Green et al. | |
| 5,211,655 | 5/1993 | Hasson | 606/205 |
| 5,275,607 | 1/1994 | Lo et al. | 606/170 X |
| 5,289,963 | 3/1994 | McGarry et al. | |
| 5,306,284 | 4/1994 | Agee et al. | 606/170 |
| 5,312,410 | 5/1994 | Miller et al. | |
| 5,318,221 | 6/1994 | Green et al. | |
| 5,330,502 | 7/1994 | Hassler et al. | 606/170 X |
| 5,366,466 | 11/1994 | Christian et al. | 606/170 X |
| 5,403,342 | 4/1995 | Tovey et al. | |
| 5,409,478 | 4/1995 | Gerry et al. | |
| 5,411,519 | 5/1995 | Tovey et al. | |
| 5,431,675 | 7/1995 | Nicholas et al. | 606/170 |
| 5,458,579 | 10/1995 | Chodorow et al. | 606/167 X |
| 5,478,350 | 12/1995 | Kratsch et al. | |
| 5,489,292 | 2/1996 | Tovey et al. | |

*Primary Examiner*—Michael Buiz
*Assistant Examiner*—Nancy Mulcare

[57] ABSTRACT

An apparatus for use in minimally invasive surgery includes an actuator slidably attached to the non-endoscopic housing, the actuator being movable between a distal position and a proximal position along the longitudinal axis of the instrument in response to user applied pressure.

20 Claims, 11 Drawing Sheets

ENDOSCOPIC SURGICAL APPARATUS WITH LONGITUDINAL ACTUATION

BACKGROUND

1. Technical Field

The present apparatus relates to an apparatus for performing an operation on body tissue, and more specifically to an apparatus for use in minimally invasive surgical procedures.

2. Background of the Art

Minimally invasive surgery and instruments for use in such surgery are well known in the art. Generally, minimally invasive surgery involves the use of instruments with relatively long narrow operating portions which may be deployed through small incisions in the skin, or through cannulas inserted through small incisions in the skin. Usually, a few such incisions are made to accommodate operating instrumentation and viewing instrumentation such as fiber optics and cameras. In some types of surgery, for example laparoscopic surgery, the operation is performed in the abdominal cavity, which is typically insufflated with a biologically inert gas to facilitate the surgical procedure. Instruments used in such surgery are required to have a seal to prevent entry or egress of fluids or other matter from the body. Because endoscopic surgery is commonly used, the term "endoscopic" is used herein to broadly refer to all types of minimally invasive surgery, including laparoscopic and arthoroscopic surgery.

Generally, the instrumentation used in endoscopic procedures has an endoscopic portion, i.e., the portion which is inserted through the cannula or incision to perform the operation in the interior of the body, and a non-endoscopic portion, usually a body portion having a handle and one or more actuators, such as triggers, buttons, rotary knobs, levers, switches, and the like. Typically, primary actuators for actuating the distal operating portion of the apparatus, i.e. clamps, retractors, fastener appliers, and the like, are triggers or levers which are pivotally attached to the body portion. Pivoting motion of these actuators, therefore, is what effects actuation of the instrument.

It would be advantageous to have an instrument which employs an alternative type of actuating motion, preferably an instrument which is ergonomically designed to more efficiently utilize the natural configuration and movements of the human hand.

SUMMARY

An apparatus is provided herein for use in minimally invasive surgery. The apparatus comprises an endoscopic portion and a non-endoscopic portion. The endoscopic portion includes an elongated tubular member defining a longitudinal axis, and an operating portion positioned at the distal end thereof. The non-endoscopic portion has a housing and at least one actuator slidably attached to the housing. The actuator is movable between a distal position and a proximal position along the longitudinal axis in response to user applied pressure.

The actuator may be resiliently biased to the distal position and preferably includes an axial bore through which the endoscopic portion is disposed.

The apparatus may also include a cauterization electrode and may accomplish irrigation of internal body tissue.

BRIEF DESCRIPTION OF THE DRAWINGS

Various embodiments are described herein with reference to the drawings, wherein:

FIGS. 6B, 6C, and 6D are, respectively, top end, and bottom views of the handle portion of the alternative embodiment shown in FIG. 6a.

DETAILED DESCRIPTION OF PREFERRED EMBODIMENT(S)

As used herein the term "distal" refers to a direction towards the patient and the term "proximal" refer to a direction away from the patient and towards the surgeon or instrument operator.

Figure 1:
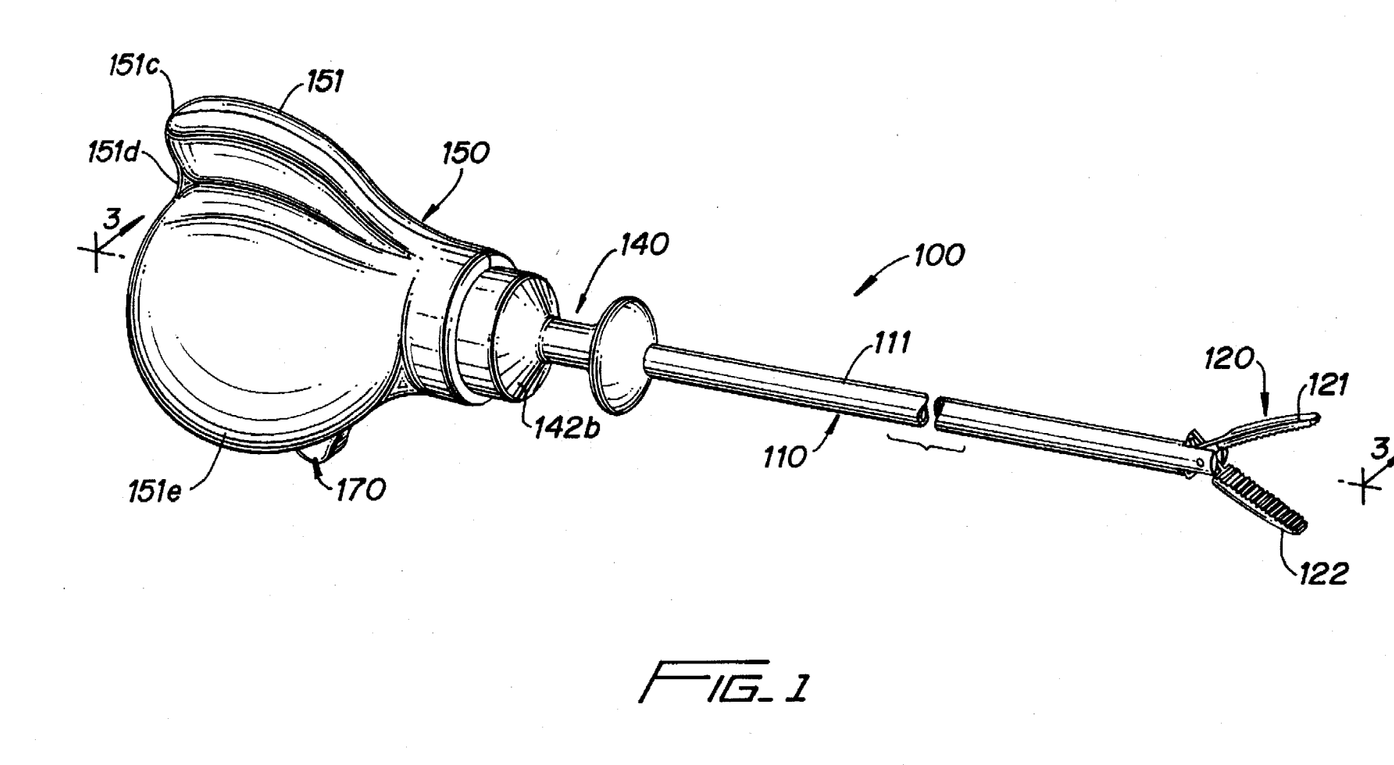
FIG. 1 is a perspective view of the apparatus.

Referring to FIG. 1, the apparatus 100 is shown wherein the endoscopic portion 110 is operably connected to the nonendoscopic portion 150. The endoscopic portion 110 includes an outer tube 111 to which a distal operating portion 120, i.e. clamping jaws 121 and 122 are pivotally attached. The non-endoscopic portion includes an ergonomically shaped housing 151, a primary actuator 140, a release trigger 170, and internal linkages and drive mechanisms as described in more detail below.

Figure 2:
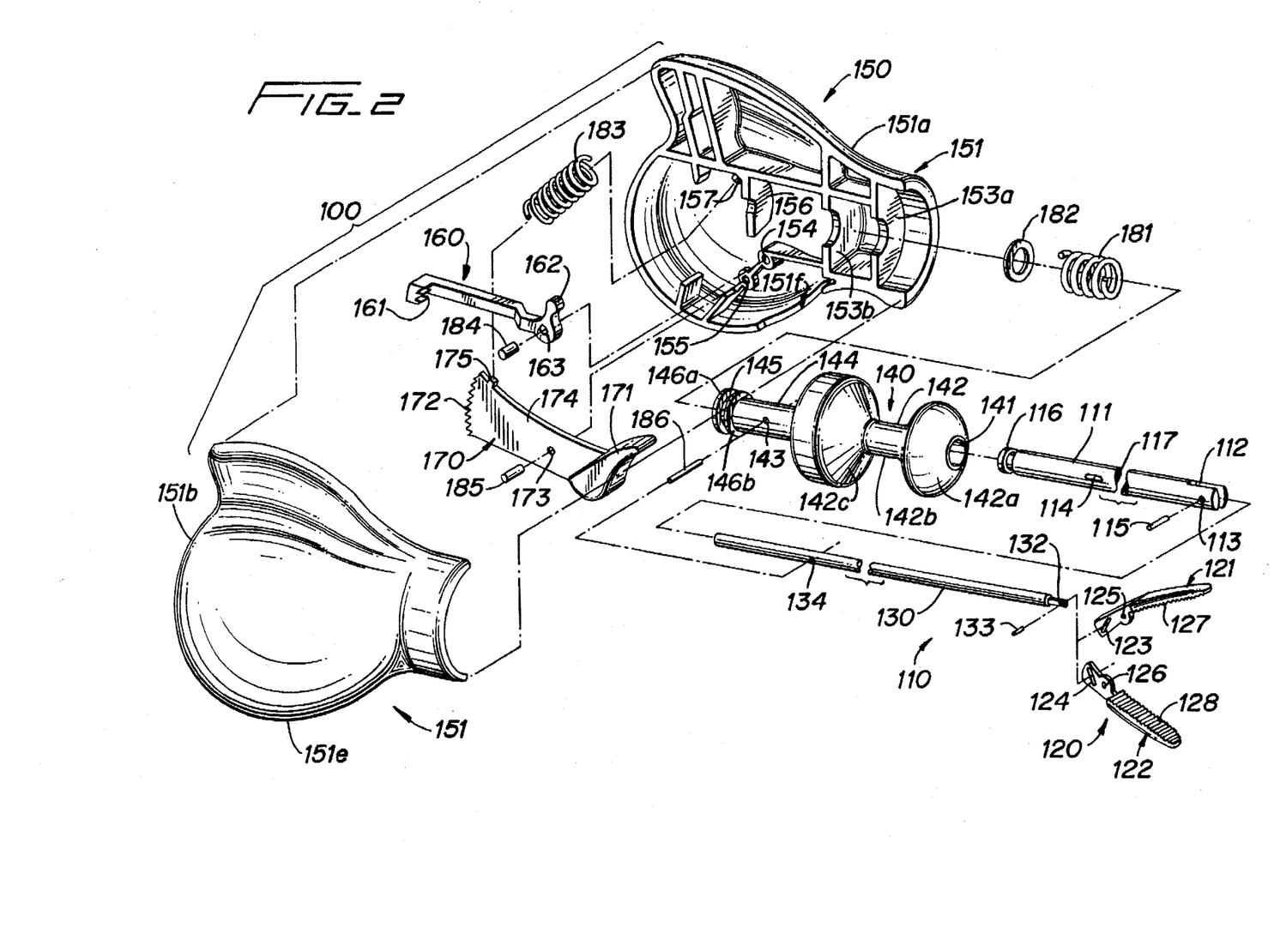
FIG. 2 is an exploded perspective view of the apparatus.

Referring additionally now to FIG. 2, the distal operating portion 120 in this embodiment comprises grasper jaws 121 and 122. Other types of operating mechanisms which are known in the art may alternatively be employed. For example, the distal operating portion may comprise clip or staple appliers, tissue cutters, forceps, needle holders, scissors, retractors, and the like.

Jaws 121 and 122 are pivotally mounted within distal slot 112 of the outer tube 111 by means of a pivot pin 115, which is disposed through aperture 113 in the outer tube and apertures 125 and 126 of the jaws.

The jaws 121 and 122 also have, respectively, elongated apertures 123 and 124 positioned at the proximal end portion of the jaws. A pin 133, disposed through aperture 132 of the drive rod 130, as well as apertures 123 and 124 of the jaws, operatively connects the distal operating portion 120 to the drive rod 130 such that proximal movement of the drive rod effects closure of the jaws 121 and 122. The jaws 121 and 122 include serrated tissue contacting surfaces 127 and 128, respectively, for securely gripping body tissue.

The outer tube 111 is an elongated tube having an axial bore 117 through which drive rod 130 is slidably disposed. The diameter of the outer tube is of such dimension as to permit insertion of the outer tube through a trocar cannula.

The proximal end portion of outer tube 111 is disposed within axial bore 141 of the primary actuator 140.

Outer tube 111 also possesses an elongated slot 114 which is longitudinally oriented and adapted to receive a pin 186 which connects the primary actuator 140 to the drive rod 130, as explained below. Also, the outer tube 111 has a circumferential notch 116 which is adapted to engage a corresponding mounting support 156 to maintain the outer tube in a fixed position relative to the non-endoscopic portion 150.

Drive rod 130 is slidably disposed within bore 117 of the outer tube and is attached at its distal end to the distal operating portion 120 by means of pin 133.

Drive rod 130 also possesses an aperture 134 for receiving pin 186, which is disposed through slot 114 in the outer tube, and which connects the primary actuator 140 to the drive shaft 130.

The primary actuator 140 is slidably mounted to the housing 151 and is longitudinally movable between a distal position in which the distal operating portion 120 is inactivated (i.e. jaws 121, 122, are open), and a proximal position in which the distal operating portion 120 is actuated (i.e. jaws 121 and 122 are closed).

The primary actuator 140 includes a hollow bore 141 through which outer tube 111 is disposed. A rear shaft portion 144 is slidably mounted to the interior of the housing 151 by means of supports 153a and 153b. At the proximal end thereof, the primary actuator 140 includes a circumferential notch portion 145 defined by spaced apart radial flanges 146a and 146b. An aperture 143 in the shaft portion receives pin 186, which extends through elongated slot 114 in the outer tube and is disposed through aperture 134 in the drive rod, thereby operatively connecting the primary actuator 140 to the drive rod 130. Thus, movement of the primary actuator 140 effects movement of the drive rod 130 and actuation of the distal operating portion 120.

The primary actuator 140 has a generally hourglass shaped distal portion 142 having a distal wide diameter portion 142a, a proximal wide diameter portion 142c, and, a relatively narrow middle portion 142b. The proximal wide diameter portion 142c includes a surface for contact by the user's fingers.

Figure 3:
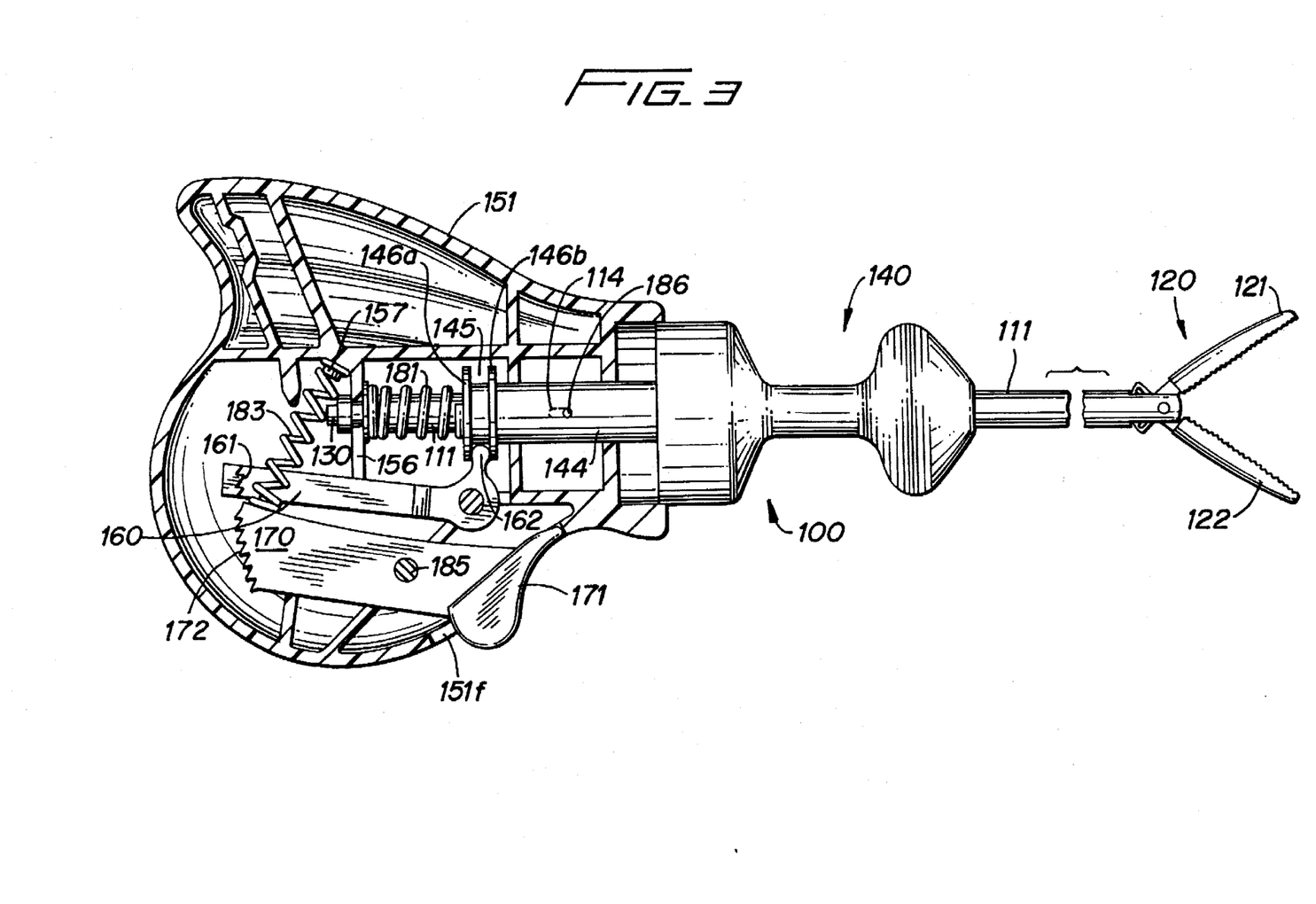
FIG. 3 is a cut-away partly sectional side elevational view of the apparatus in an initial open configuration.

The primary actuator 140 moves longitudinally rearward (i.e. proximally) in response to pressure applied by the user's fingers to the proximal wide diameter portion 142c. The user applied pressure must be sufficient to overcome the force of spring 181, which biases the primary actuator 140 to the unactuated distal position. Referring briefly to FIG. 3, helical compression spring 181 is mounted around outer tube 111 and is disposed between mounting support 156 of the housing and radial flange 146a of the primary actuator. Washer 182 provides backing for the spring 181.

Referring again to FIG. 2, primary actuator 140 may also be rotated around the axis of the instrument as defined by the endoscopic portion 110 in order to accomplish rotation of the endoscopic portion 110.

Rocker arm 160 is pivotally mounted to the interior of housing 151 by means of pin 184 disposed through aperture 163 of the rocker arm 160 and in aperture 154 of the housing 151.

Rocker arm 160 has a projection 162 at one end which engages slot 145 of the primary actuator. At its other end rocker arm 160 includes a pawl 161. Rocker arm 160 pivots counterclockwise around pin 184 in response to proximal movement of primary actuator 140.

Release trigger 170 is pivotally mounted to housing 151 by means of pin 185 disposed through aperture 173 of the trigger and in aperture 155 of the housing. Release trigger 170 includes a finger rest 171 attached to one end of a flat plate 174. At the other end of flat plate 174 is a vertical array of ratchet teeth 172 extending along the proximal edge thereof. A helical compression spring 183 is mounted between the upper edge of plate 174 in the vicinity of the rear edge, and a mounting post 157 in the housing 151. A corresponding mounting post 175 is located on the release trigger to maintain the spring 183 in the proper position. The finger rest 171 is disposed through aperture 151f of the housing and is positioned exterior to the housing 151 such that a user may pivot the release trigger clockwise (as shown) against the biasing force of spring 183 by applying downward pressure on finger rest 171.

Housing 151 may be fabricated in two halves 151a and 151b adopted to be fitted together. Optionally, pins 184 and 185 can be integrally fabricated as part of housing half 151a and 151b by, for example, injection molding. The exterior surface of housing 151 is ergonomically shaped for conformity with the natural configuration and movement of the human hand.

Figure 1A:
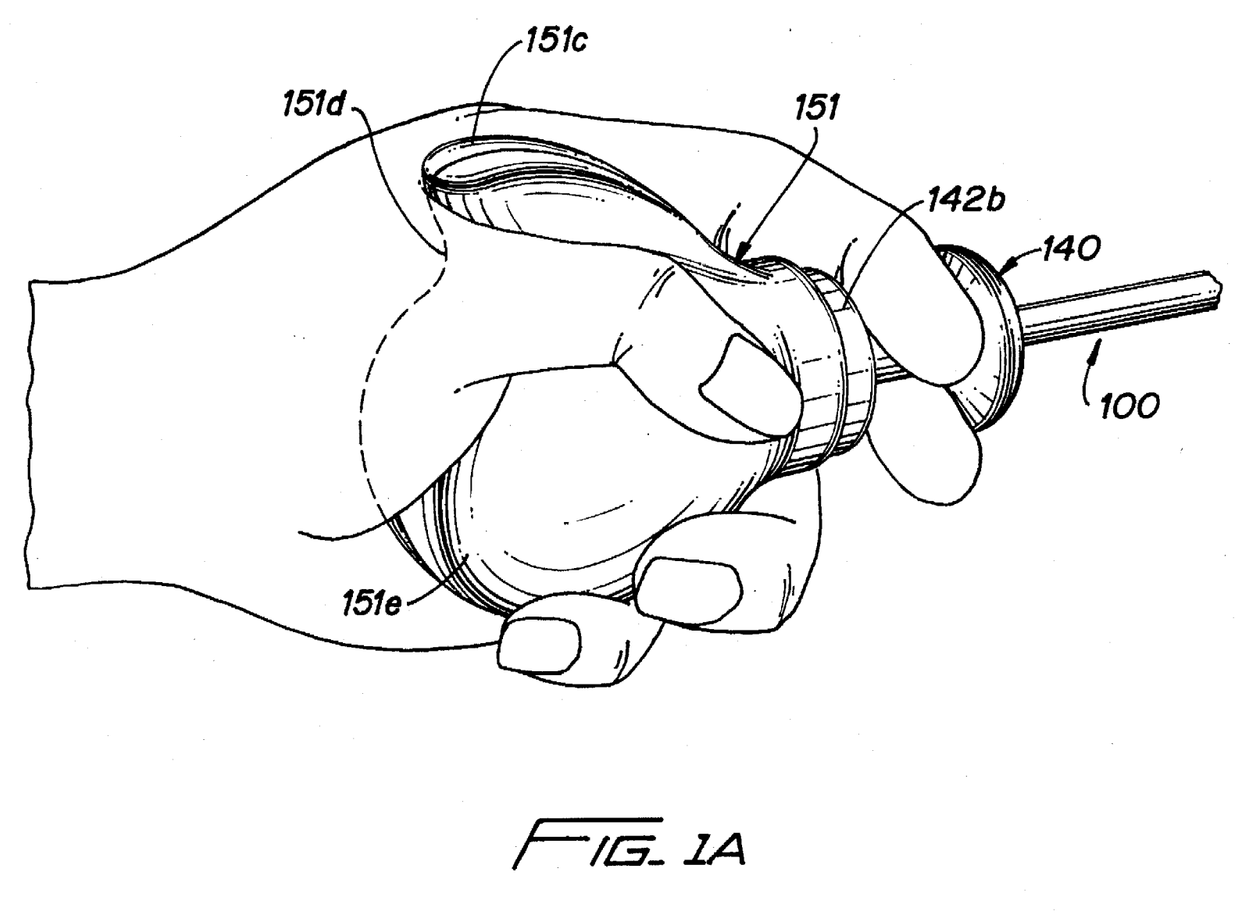
FIG. 1A is a side view illustrating how the apparatus is held by a user.

Referring to FIGS. 1 and 1A the housing 151 includes a bulbous portion 151e configured and dimensioned to fit within the palm of the human hand. Incurvate portion 151d is adapted to fit within the crook of the human hand between the thumb and the forefinger. Pinky support 151k is a projection having a curved distal surface for receiving the pinky and is an optional feature which provides for a more stable and secure gripping by a human hand. Elongated portion 151c is adapted to stabilize the position of the hand relative to the housing 151. The forefinger and middle finger of the hand curve around front and are positioned in the middle portion 142b of the actuator 140. The user actuates the apparatus by pulling back the primary actuator 140 with these fingers. The ring finger may be used to actuate the release trigger 170. The apparatus is more closely aligned with the user's forearm and the user's wrist can remain straight. This permits the surgeon to use the strength of the forearm to manipulate and align the apparatus in the initial unactuated condition with jaws 121, 122 in the open configuration.

Referring now to FIG. 3 the apparatus 100 is shown in the initial open configuration. Jaws 121 and 122 are spaced apart so as to permit body tissue to be positioned therebetween. The actuator 140 is in a distal position to which it is biased by spring 181. Rocker arm 160 is optionally positioned such that pawl 161 is higher than the proximal end of the release trigger 170. Alternatively, the teeth of pawl 161 can be engaged with the proximal end of release trigger 170, the pawl teeth 161 being easily movable in a downward direction relative to the proximal end of the release trigger but resistant to movement in the opposite direction until disengaged.

Figure 4:
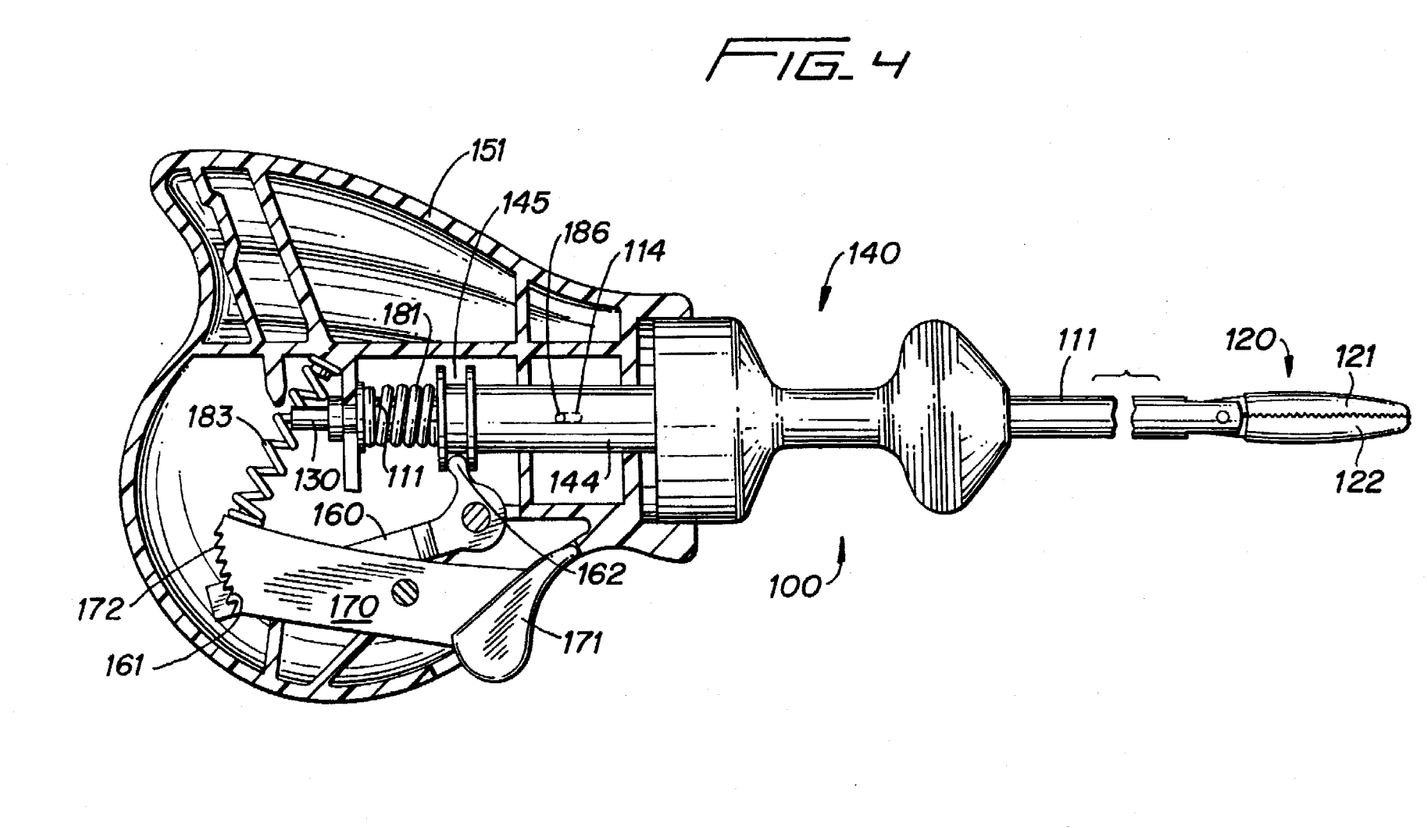
FIG. 4 is a cut-away partly sectional side elevational view of the apparatus in a closed and locked configuration.

In FIG. 4, the primary actuator 140 has been moved proximally backward. Pin 186, which extends through slot 114 of the outer tube and into aperture 134 of the drive rod 130, enables the motion of the primary actuator 140 to be transferred to the drive rod 130 to close the jaws 121, 122.

As can be seen in FIG. 4, when the primary actuator 140 is moved proximally rocker arm 160 is pivoted counterclockwise (as shown) such that the proximal pawl 161 engages the ratchet teeth 172 of the release trigger. The release trigger 170 is biased to its initial position by compression spring 183. Thus, the rocker arm 160 maintains the position as shown in FIG. 4 even after the surgeon releases pressure on the primary actuator 140. The jaws 121, 122, therefore, remain closed unless the release trigger 170 is actuated.

Figure 5:
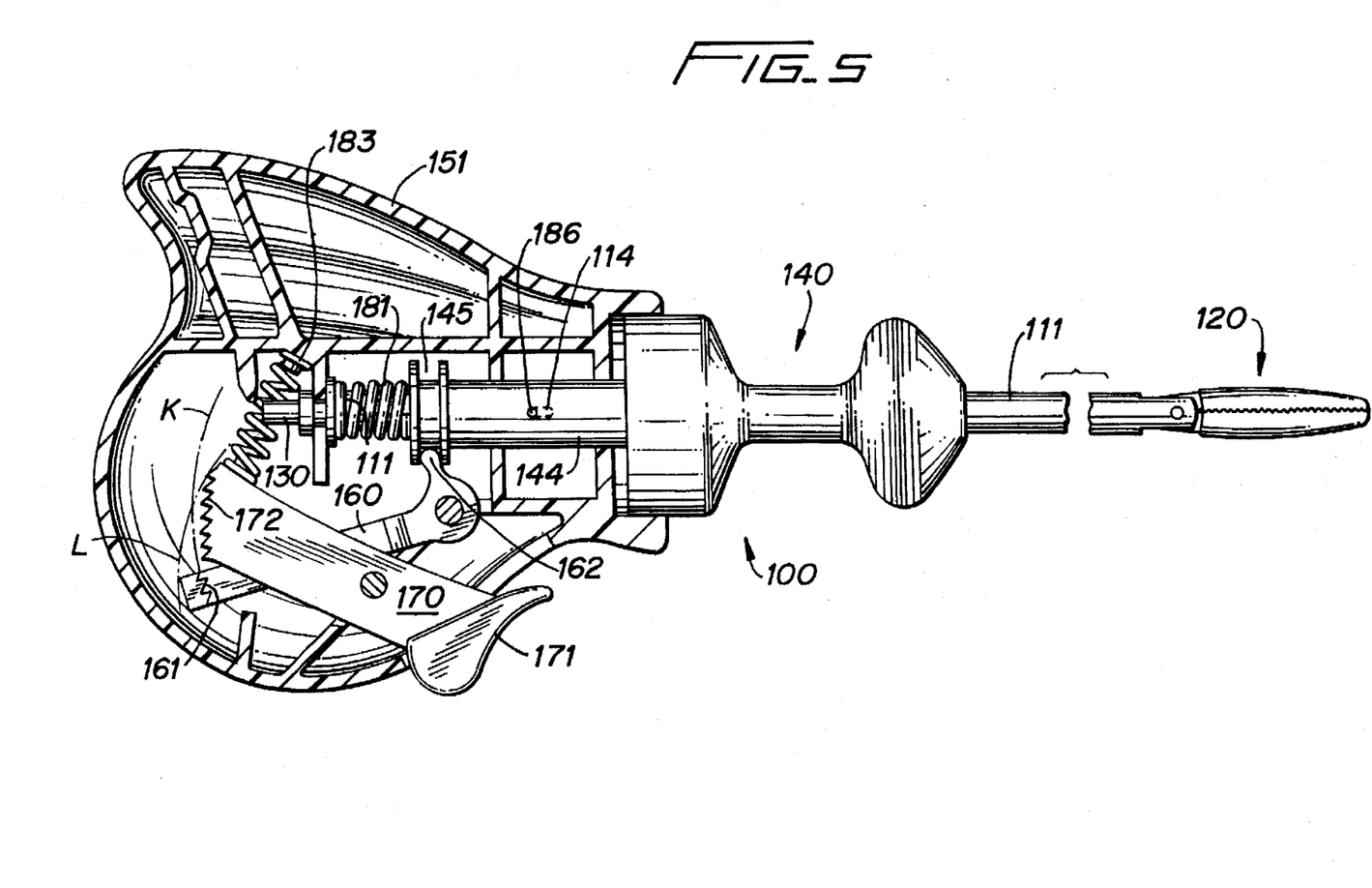
FIG. 5 is a cut-away partly sectional side view of the apparatus in an intermediate configuration.

Referring now to FIG. 5, the release trigger 170 is actuated by pressing downward on the finger rest 171. This moves the proximal end of the release trigger upward against the biasing force of spring 183. Because the rocker arm 160 and the release trigger 170 are pivotally moved, the ratchet teeth 172 and the pawl 161 of the rocker arm travel along arcs. As shown in FIG. 5, arc K is the path travelled by the pawl 161; arc L is the path travelled by the ratchet teeth 172. These arcs have a region wherein they intersect, so as to permit the pawl 161 and the ratchet teeth 172 to engage (see, FIG. 4). However, because the radius of curvature of the arcs differ, and because the pivot points 185 and 184 are spaced apart from each other, arcs K and L also have regions wherein they do not intersect and wherein there can be no engagement between the pawl 161 and the ratchet teeth 172. The arc L traveled by the ratchet teeth 172 has a shorter radius than arc K of the pawl 161. Thus, the ratchet teeth 172 disengage from the pawl 161 when the release trigger 170 is pressed, thereby releasing the rocker arm 160 and permitting the primary actuator 140 to move distally under the biasing force of compression spring 181. Consequently, the drive rod 130 moves forward and jaws 121, 122 reopen.

Figures 3A, 3B:
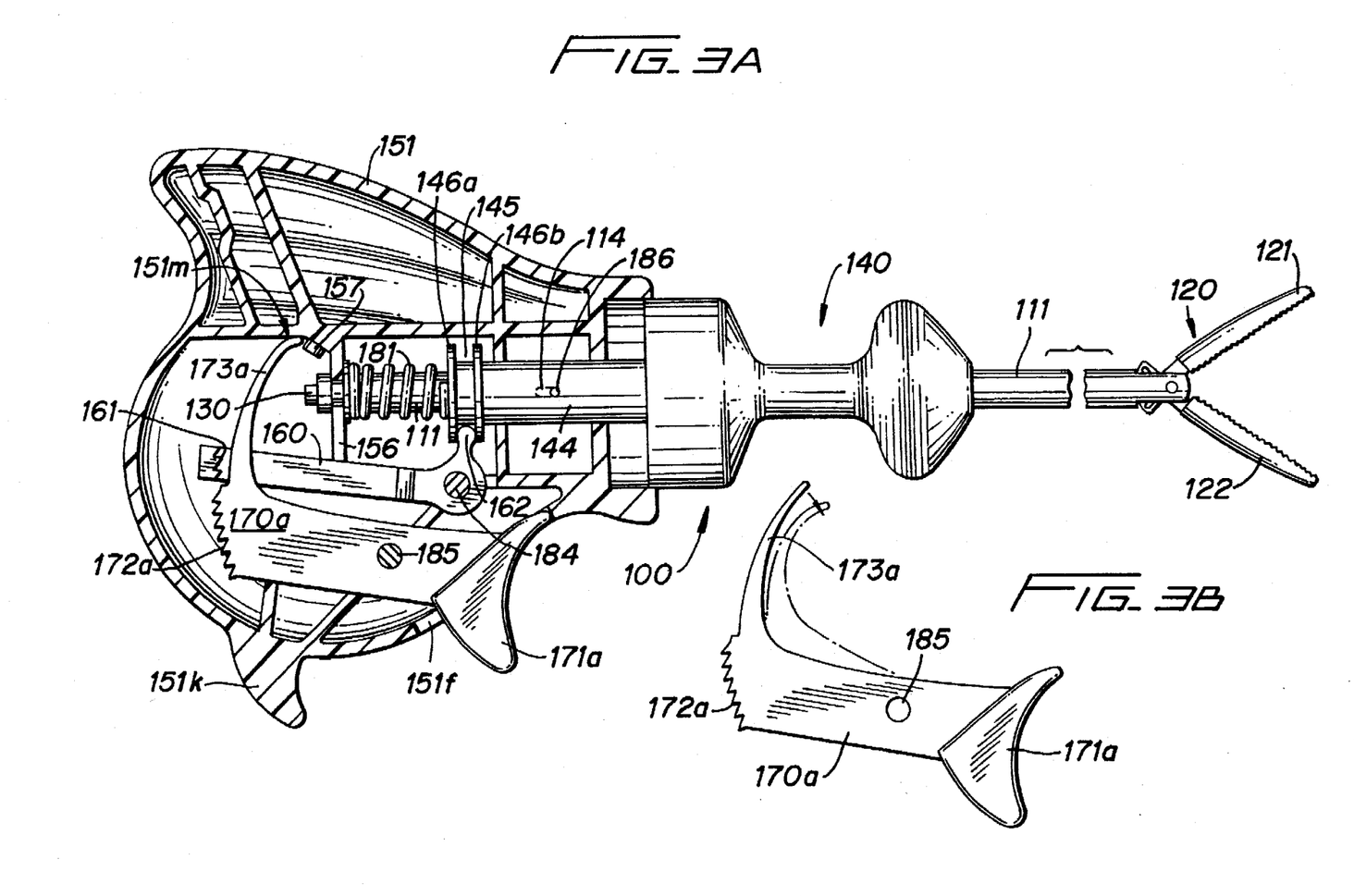
FIG. 3A is a cut away partly sectional side elevational view of the apparatus showing an alternative embodiment of the trigger.
FIG. 3B is a side elevational view of an alternative embodiment of the trigger.

Referring to FIGS. 3A and 3B, an alternative embodiment 170a of the trigger is shown, which includes a finger rest 171a, flat plate 174a, ratchet teeth 172a, and an integrally fabricated resilient projection 173a which serves as a spring to bias the proximal end portion of release trigger 170a in a manner similar to that of spring 183 discussed above. The release trigger 170a can be fabricated from a suitable polymeric material by injection molding. Release trigger 170a is preferably positioned as shown in FIG. 3A with the upper end portion of the resilient projection 173a abutting wall 151m in the interior of housing 151. Spring 183 is eliminated, thereby reducing construction costs. When the release trigger 170a is actuated the resilient projection 173a will flex as shown in FIG. 3B while providing a resilient biasing force to return the trigger 170a to the unactuated position.

Figure 6A:
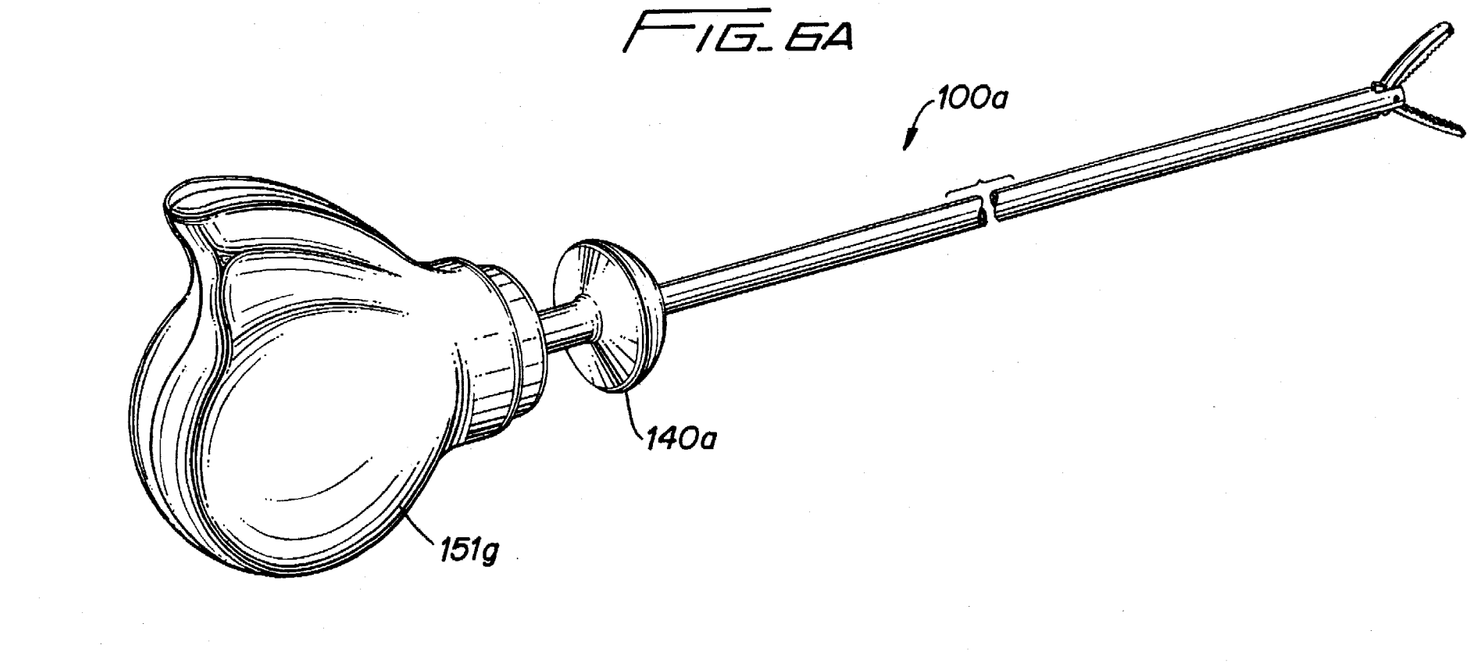
FIG. 6A is a perspective view of an alternative embodiment of the apparatus.
Figure 6B:
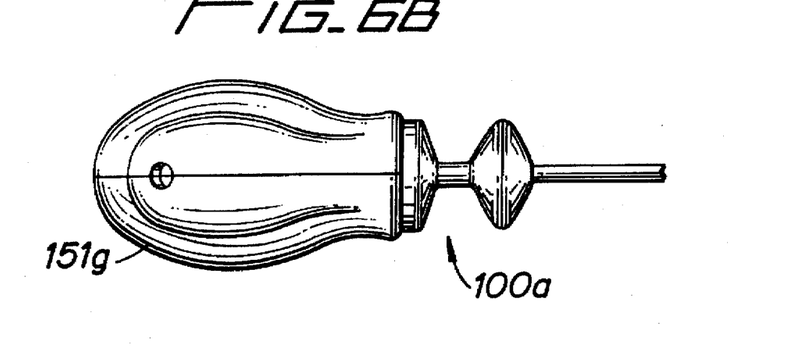
Figure 6C:
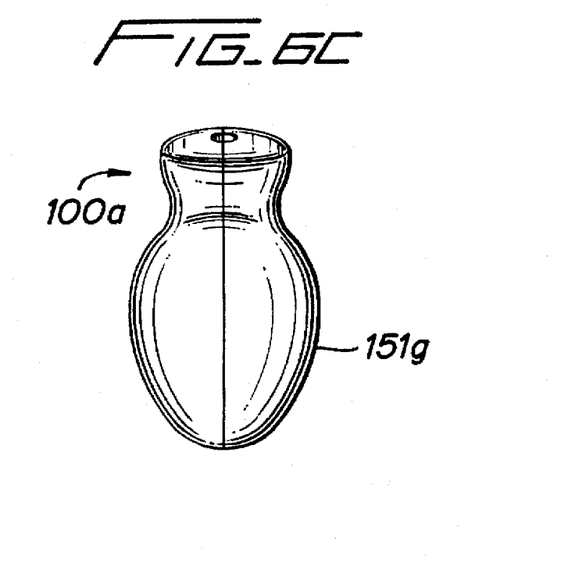
Figure 6D:
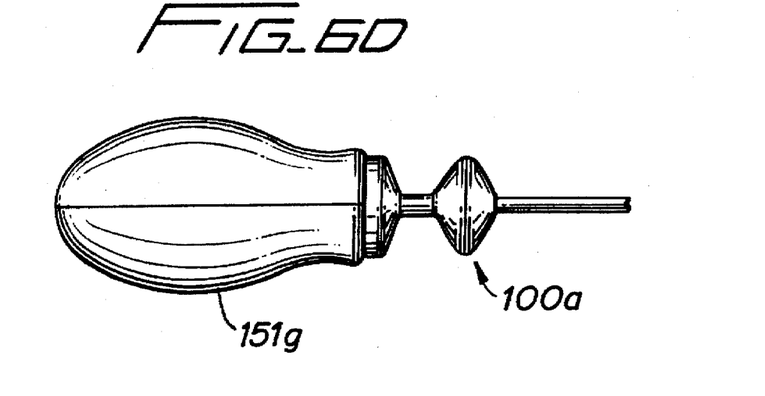

The use of a release trigger is an optional feature. FIGS. 6A, 6B, 6C, and 6D are views of an apparatus 100a which is similar to that of apparatus 100 except that apparatus 100a does not employ a release trigger. When the primary actuator 140 is no longer pressed, the distal operating portion automatically resumes its initial configuration or function. Housing 151g is similar to housing 151 of apparatus 100 in all respects except that it has no opening such as 151f for a trigger. As shown in FIGS. 6A the housing 151g does not include a pinky support 151k. However, pinky support 151k can optionally be provided on housing 151g for added gripping stability.

Figures 7, 7A:
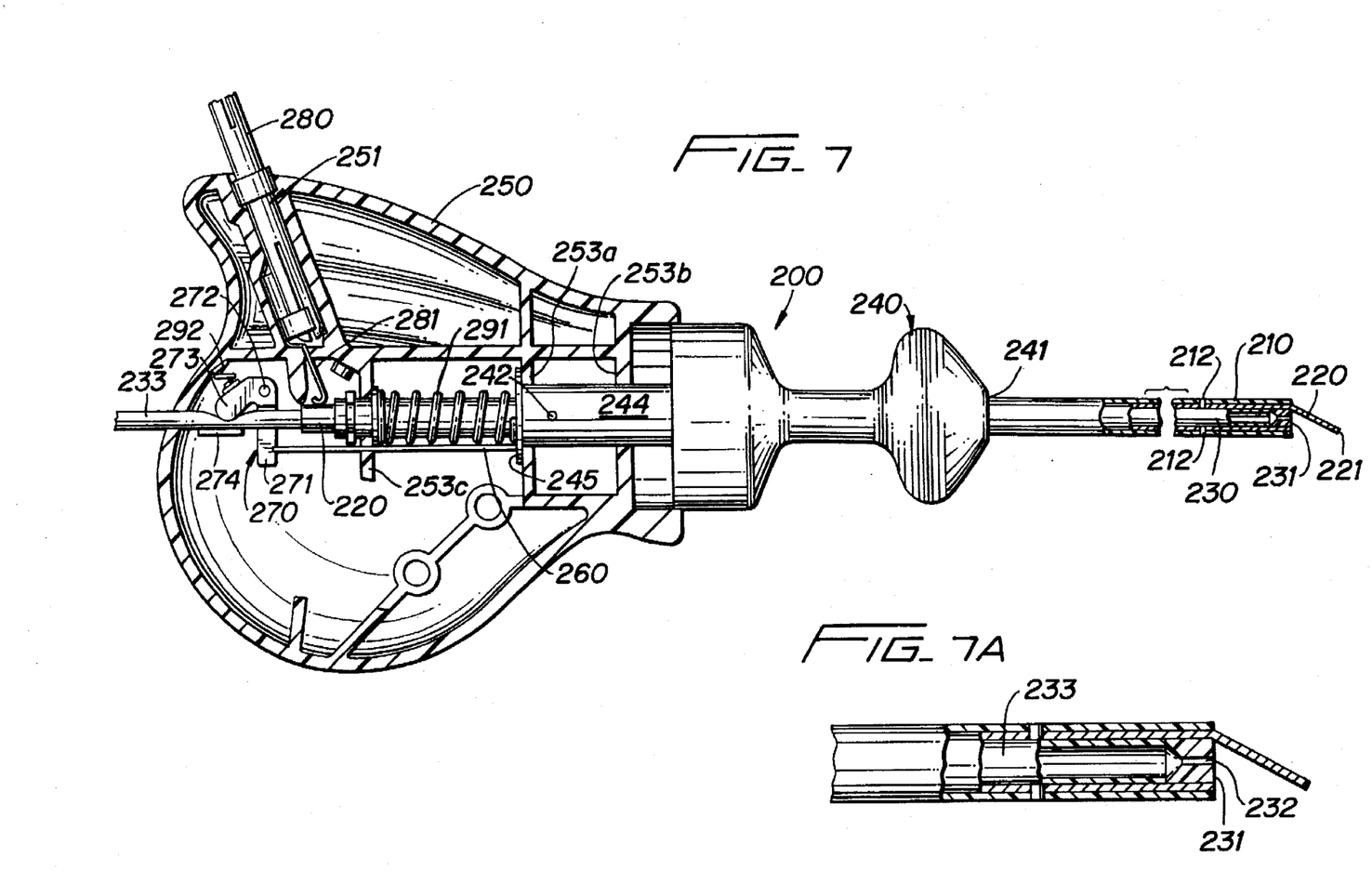
FIG. 7 is a partially sectional side elevational view of irrigator apparatus.
FIG. 7A is a sectional side elevational view of the distal tip of the irrigator.
Figures 8, 9:
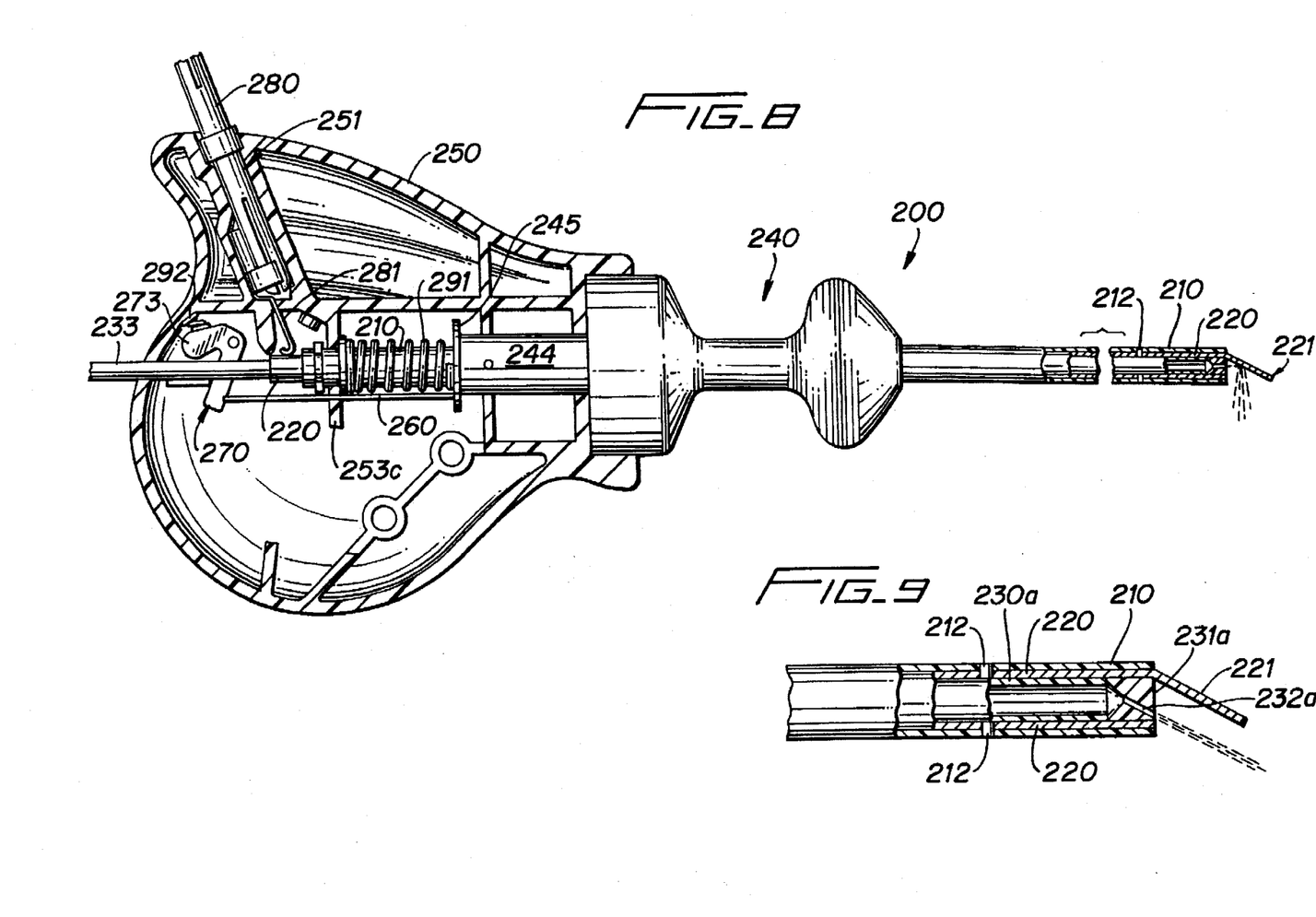
FIG. 8 is a partly sectional side elevational view of the irrigator apparatus in operation.
FIG. 9 is a partly sectional side elevational view of an alternative irrigator tip.

FIGS. 7, 7A, and 8 illustrate an alternative embodiment, apparatus 200, which is a cautery/irrigator device. Referring to FIGS. 7 and 7A, the endoscopic portion includes an outer tube 210, an electrocautery electrode 220 and irrigation tube. More specifically, the outer tube 210 comprises an elongated member having an axial bore through which the electrode 220 is disposed. At its proximal end outer tube 210 is rotatably mounted within housing 250. Outer tube 210 is also disposed within an axial aperture 241 of the primary actuator 240. The outer tube 210 is preferably fabricated from an electrically insulating material such as plastic or is at least coated with an insulator.

The electrode 220 is a tubular member which extends through the bore of the outer tube. The electrode 220 has a distal applicator tip 221 which is angled from the longitudinal direction.

The irrigation tube 230 extends through the bore of the electrode 220 and terminates in a nozzle 231 having an orifice 232 through which the irrigation fluid (e.g. saline solution) is dispensed. Orifice 232 is shown as being aligned with the axis of the instrument so as to direct a stream of fluid against the underside of the electrode tip 221. However, alternative orientations of orifice 232 are also useful, as explained below. Irrigation tube 230 is fabricated from a flexible and resilient tubular material which can be clamped shut by transversely applied pressure to prevent the flow of fluid therethrough.

Primary actuator 240 actuates the irrigation function. It is slidably mounted to housing 250 and is longitudinally movable between an initial unactuated distal position in which the flow of irrigation fluid is inhibited, and a proximal actuated position in which the flow of fluid is released.

The primary actuator 240 includes a hollow bore 241 through which outer tube 210 is disposed. A rear shaft portion 244 is slidably mounted to the interior of the housing 250 by means of supports 253a and 253b. At the proximal end thereof the primary actuator 240 includes a flange 245.

Helical compression spring 291 is disposed around the portion of the outer tube 210 which extends proximally beyond the rear of the primary actuator 240. The distal end of spring 291 abuts flange 245. Spring 291 is backed at its proximal end by mounting support 253c. Spring 291 biases the primary actuator 240 to the distal unactuated position.

The proximal end portion of the outer tube 210 is rotatably mounted to mounting support 253c. Pin 242 disposed laterally through the actuator 240 and the outer tube 210 enables the user to rotate the outer tube 210 and the electrode by turning the actuator 240. The tubular electrode 220 is linked to outer tube 210 by pins 212 and extends proximally beyond the proximal end of the outer tube 210 to present a surface for electrical connection.

The housing has a chamber 251 into which cautery electrode 280 is disposed. Cautery electrode 280 includes a metal clip 281 which makes contact with the proximal end portion of the tubular electrode 220. Cautery electrode is electrically connected to a suitable source of electric power. When the power source is switched on, the apparatus provides the surgeon with monopolar cauterization facility to cut or seal body tissue by contacting the body tissue with applicator tip 221..

Clamp 270 is pivotally mounted at pivot pin 272 to the housing and possesses a lower arm 271 and a contact member 273. Helical compression spring 292 biases the contact member 273 downward (as shown) into contact with flexible irrigation fluid supply tube 233, thereby closing the tube 233.

Connecting rod 260 connects lower arm 271 of the clamp 270 to the flange 245 of the primary actuator 240.

Referring to FIG. 8, when the primary actuator 240 is actuated, connecting rod 260 pivots the clamp 270 clockwise (as shown) against the biasing force of spring 292 thereby permitting irrigation supply tube 233 to resiliently open. A jet of irrigation fluid thereupon flows out of nozzle 231 through orifice 232, as shown in FIG. 8.

FIG. 8 illustrates a jet of fluid directed against the side of the angled tip 221 of the cautery electrode.

Referring to FIG. 9, an alternative embodiment is shown wherein irrigation tube 230a includes nozzle 231a having an orifice 232a which is angled so as to direct the jet of irrigation fluid parallel to the angled tip 221.

It will be understood that various modifications may be made to the apparatus disclosed herein. For example, one skilled in the art will readily appreciate that a cauterization facility may also be incorporated into apparatus 100, and a pinky support such as 151k can be provided on the housing of any of the apparatus embodiments described hereinabove. Therefore, the above description should not be construed as limiting, but merely as exemplifications of preferred embodiments. Those skilled in the art will envision other modifications within the scope and spirit of the claims appended hereto.

What is claimed is:

1. An apparatus for use in minimally invasive surgery, which comprises
   a) an endoscopic portion including an elongated tubular member defining a longitudinal axis, and an operating portion positioned at the distal end thereof, and
   b) a non-endoscopic portion having a housing and at least one actuator slidably attached to said housing, said actuator being movable between a distal position and a proximal position along said longitudinal axis in response to user applied pressure, and said actuator having a relatively wide diameter proximal portion with a distal facing surface for contact with a user's finger, and a relatively narrow middle portion into which the user's finger is received.

2. The apparatus of claim 1 wherein said actuator is resiliently biased to said distal position.

3. The apparatus of claim 1 wherein said actuator has an axial bore.

4. The apparatus of claim 3 wherein said elongated tubular member of said endoscopic portion is disposed through said actuator bore.

5. The apparatus of claim 1 wherein said actuator presents a surface for actuation by the forefinger and middle finger of a user's hand.

6. An apparatus for use in minimally invasive surgery which comprises:
   a) an endoscopic portion including an elongated tubular member defining a longitudinal axis, and an operating portion positioned at the distal end thereof, and
   b) a non-endoscopic portion having a housing and at least once actuator slidably attached to said housing, said actuator being movable between a distal position and a proximal position along said longitudinal axis in response to user applied pressure, wherein said actuator presents a surface for actuation by the forefinger and middle finger of a user's hand, and wherein said actuator is generally hourglass shaped.

7. The apparatus of claim 1 wherein said operating portion comprises a mechanism selected from the group consisting of graspers, scissors, forceps, clip appliers, staple appliers, tissue cutters, and retractors.

8. The apparatus of claim 1 wherein said actuator is rotatable.

9. The apparatus of claim 1 wherein said endoscopic portion includes a drive rod operatively connected to said actuator and said operating portion.

10. The apparatus of claim 2 further comprising:
    a release trigger movable between an initial position and a release position; and
    a rocker arm connected to said actuator and movable from a first position to a second position in response to movement of said actuator from said distal position to said proximal position, said rocker arm engaging said release trigger when said rocker arm is in said second position and said release arm is in said initial position, said rocker arm being disengaged from said release trigger in response to movement of said release trigger to said release position.

11. The apparatus of claim 10 wherein said release trigger is resiliently biased to said initial position and movable to said release position in response to user applied force.

12. The apparatus of claim 11 wherein said release trigger includes a resilient projection integrally fabricated therewith for providing a resilient biasing force.

13. The apparatus of claim 10 wherein said rocker arm and said release trigger are pivotally mounted to said housing.

14. The apparatus of claim 1 further including a cauterization electrode.

15. The apparatus of claim 14 further including an irrigation tube.

16. The apparatus of claim 15 further including a clamp for closing said irrigation tube, said clamp being movable between a first position in which said irrigation tube is closed and a second position wherein said irrigation tube is open, said clamp being resiliently biased to said first position and movable to said second position in response to movement of said actuator from said distal position to said proximal position.

17. The apparatus of claim 1 wherein said housing has a bulbous portion configured and dimensioned to fit within the palm of a human hand.

18. The apparatus of claim 10 wherein said housing includes an incurvate portion adapted to engage the crook of a human hand between the thumb and the forefinger.

19. The apparatus of claim 18 wherein said housing includes a pinky support.

20. The apparatus of claim 19 further including a release trigger pivotally movable between an initial position and a release position, wherein said actuator is generally hourglass shaped and rotatable with respect to said housing.

* * * * *